(12) United States Patent
Shang et al.

(10) Patent No.: US 10,391,113 B2
(45) Date of Patent: Aug. 27, 2019

(54) COMPATIBLE COMPOSITION CONTAINING CHINESE MEDICINE CICHORIUM GLANDULOSUM BOISS ET HOUT AS LIPID-LOWERING ACTIVE INGREDIENT

(71) Applicant: Nanjing Ruiying Runze Biopharmaceutical Technology Co., Inc., Nanjing, Jiangsu (CN)

(72) Inventors: Jing Shang, Jiangsu (CN); Lin Ding, Jiangsu (CN); Guohong Qin, Jiangsu (CN); Tao Wang, Jiangsu (CN); Jun Liu, Jiangsu (CN); Yu Li, Jiangsu (CN); Ting He, Jiangsu (CN)

(73) Assignee: NANJING RUIYING RUNZE BIOPHARMAEUTICAL TECHNOLOGY CO., INC., Nanjing, Jiangsu (CN)

(*) Notice: Subject to any disclaimer, the term of this patent is extended or adjusted under 35 U.S.C. 154(b) by 78 days.

(21) Appl. No.: 15/308,852

(22) PCT Filed: Mar. 6, 2015

(86) PCT No.: PCT/CN2015/073826
§ 371 (c)(1),
(2) Date: Dec. 5, 2016

(87) PCT Pub. No.: WO2015/169122
PCT Pub. Date: Nov. 12, 2015

(65) Prior Publication Data
US 2017/0100421 A1    Apr. 13, 2017

(30) Foreign Application Priority Data

May 5, 2014    (CN) .......................... 2014 1 0186571

(51) Int. Cl.
*A61K 31/7048* (2006.01)
*A61K 31/352* (2006.01)

(52) U.S. Cl.
CPC ........ *A61K 31/7048* (2013.01); *A61K 31/352* (2013.01)

(58) Field of Classification Search
None
See application file for complete search history.

(56) References Cited

U.S. PATENT DOCUMENTS

2008/0146657 A1* 6/2008 Tsuboi ................. A61K 31/352
514/456

FOREIGN PATENT DOCUMENTS

| CN | 1803787 A | 7/2006 |
| CN | 101103121 A | 1/2008 |
| CN | 101909619 A | 12/2010 |
| CN | 102078356 A | 6/2011 |
| CN | 103977015 A | 8/2014 |

OTHER PUBLICATIONS

Yang, W. Z., Wang, H., Shang, J., Feng, F., & Xie, N. (2009). Chemical constituents from Cichorium glandulosum. 7( 3), 193-195. (Year: 2009).*
International Search Report and Written Opinion from Corresponding Application No. PCT/CN2015/073826; dated May 25, 2015.
English Translation of International Search Report from Corresponding Application No. PCT/CN2015/073826; dated May 25, 2015.

* cited by examiner

*Primary Examiner* — Shaojia A Jiang
*Assistant Examiner* — Dale R Miller
(74) *Attorney, Agent, or Firm* — Pearne & Gordon LLP

(57) ABSTRACT

Disclosed are a compound pharmaceutical composition containing *Cichorium glandulosum* Boiss et Hout as a lipid-lowering active ingredient and the use of the composition for preparing a drug for treating or preventing lipid metabolism disorders, wherein the composition comprises a pharmaceutically active ingredient and a pharmaceutically acceptable carrier, wherein the pharmaceutically active ingredient consists of quercetin-3-O-β-D-glucuronoside, isoquercitrin and quercetin at a molar ratio of 1.1-2.4:1.3-3.3:1.2-3.1.

3 Claims, 2 Drawing Sheets

COMPATIBLE COMPOSITION CONTAINING CHINESE MEDICINE CICHORIUM GLANDULOSUM BOISS ET HOUT AS LIPID-LOWERING ACTIVE INGREDIENT

BACKGROUND OF THE INVENTION

1. Field of the Invention

The present invention relates to the natural medicine field, and particularly, to the compatible composition containing the active ingredient quercetin-3-O-β-D-glucuronide, isoquercitrin and quercetin of *Cichorium glandulosum* Boiss et Hout.

2. Description of the Related Art

As well known, the morbidity of a series of lipid metabolism disorders, such as hyperlipoidemia, fatty liver, adiposity and so on is increasing along with development of economy and change of life style. It was shown in *Guidelines for prevention and treatment of dyslipidemia in Chinese adults* published in 2007 that the morbidity of dyslipidemia in China has risen to 18.6%. Recently, the morbidity of fatty liver also rapidly increases. In Europe and America, the morbidity of adult fatty liver has risen to 31% from 10% in 80's of 20th century, the morbidity of fatty liver in people with obesity and type II diabetes patients is 50%, and the morbidity of fatty liver in the alcoholist and alcoholic is 58%. However, the effect of the lipid-lowering drug clinically used now is not satisfactory, and it is urgent to develop a lipid-lowering drug.

Traditional Chinese medicine has formed distinctive theoretical system through thousands years of history, and provides a precious resources for modern research and development of Chinese medicine. However, because compound composition of the traditional Chinese medicine is complex, and quality control is difficult, thereby application of lipid-lowering Chinese medicine in broader range is limited. Component Chinese medicine can be made by removing invalid and toxic ingredients from complex Chinese medicine, extracting the active ingredients for the disease, and optimizing the ratio thereof to exert their medical effect at the highest level.

Quercetin-3-O-β-D-glucuronide, isoquercitrin and quercetin are the lipid-lowering active and effective ingredients of Chinese Medicine *Cichorium glandulosum* Boiss et Hout. Quercetin-3-O-β-D-glucuronide has obvious lipid-lowering effect, which can i) promote the oxidation of the fatty acid of the hepatocyte to decrease the content of the intracellular triglyceride and lipid droplet; ii) decrease the level of triglyceride and cholestenone in the blood plasma. Isoquercitrin can remove free radicals, inhibit the lipid peroxidation, and protect the organism from oxidation damage under hyperlipoidemia level. Quercetin can decrease the level of TNF-α and IL-6 in the hepatocyte, can reduce the expression and release of the inflammatory factor, improve insulin resistance, and promote the pathological repair in the lipid metabolism disorder. The structural formulae are as follows:

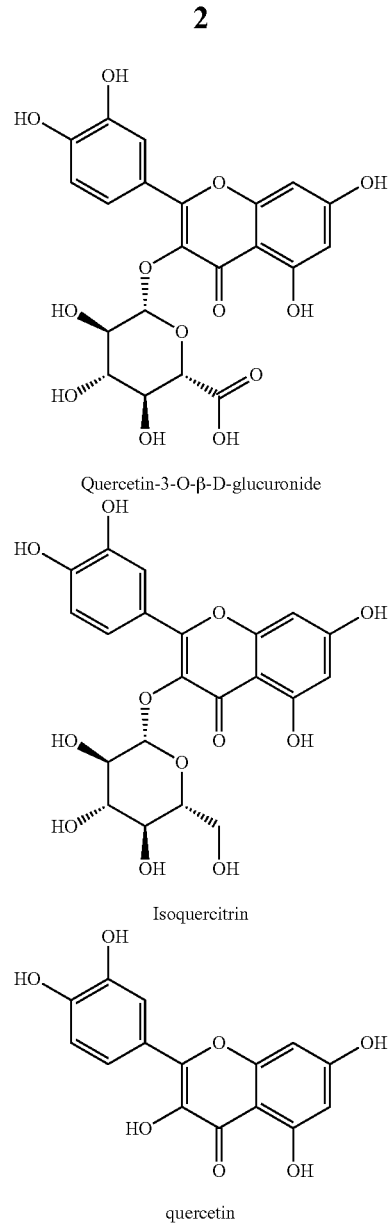

Quercetin-3-O-β-D-glucuronide

Isoquercitrin quercetin

So far, it has not yet been reported to formulate a drug by using quercetin-3-O-β-D-glucuronide, isoquercitrin and quercetin to treat the diseases of lipid metabolism disorder.

SUMMARY OF THE INVENTION

The present invention discloses a compound pharmaceutical composition, having pharmaceutical active ingredients consisting of quercetin-3-O-β-D-glucuronide, isoquercitrin and quercetin. It is proved by pharmacodynamic tests that the three ingredients, which are combined together, can treat synergistically the disease of lipid metabolism disorder, preferably, treat obesity, fatty liver, atherosclerosis, hyperlipoprotememia and so on.

Test results show that compatible composition of quercetin-3-O-β-D-glucuronide, isoquercitrin and quercetin, with a molar concentration ratio of 1.1-2.4:1.3-3.3:1.2-3.1, can obviously decrease lipid droplet content in primary hepatocyte of rats, and its lipid-lowering effect can reach 20% or more on average. Preferably, the molar ratio of the three ingredients is 1.3-2.1:1.6-3.0:1.5-2.9, and in this range, the lipid-lowering effect of the composition can reach 30% or more on average. More preferably, the molar ratio of the three ingredients is 1.4-1.9:1.8-2.6:1.8-2.6, and in this range, the lipid-lowering effect of the composition can reach 40% or more on average.

The compound pharmaceutical composition of the present invention can be made into various preparations in pharmaceutical field, such as tablet, granule, injection, dripping pill, capsule, aerosol, turunda, plaster and so on, and can be administered by oral route, or by intravenous, muscle, subcutaneous injection or other kinds of injection, or by intraoral, per rectum, per vaginam, per cutem absorption, or by intranasal inhalation, or administered in any pharmaceutical formulation containing the active ingredients, and in any pharmaceutically accepted formulation. In the composition of the present invention, in addition to the pharmaceutical active ingredients, as pharmaceutically accepted carrier, one or more pharmaceutically commonly used pharmaceutical preparation necessities can be added, such as excipient, diluents, binder, stabilizer and so on, in addition, some chemical additives can be added, such as pigment, preservative, flavoring agent and so on.

In the following, pharmacodynamic tests and results are described.

The method of preparing the compatible composition solution of the tested drug is as follows: dimethyl sulfoxide is used as the solvent and quercetin-3-O-β-D-glucuronide, isoquercitrin and quercitrin are dissolved, wherein the final concentration of dimethyl sulfoxide is less than 0.1%.

The composition solution related to the present invention is designed according to D-optimal design method, and 14 compatible groups are designed, and in each compatible group, the molar ratio of the three active ingredients is shown below.

TABLE 1 constitution of compatible compositions (molar concentration ratio)

| group number | quercetin-3-O-β- | isoquercitrin | quercitrin |
|---|---|---|---|
| 1 | 1.000 | 2.509 | 2.491 |
| 2 | 1.516 | 1.508 | 2.976 |
| 3 | 1.000 | 4.000 | 1.000 |
| 4 | 1.299 | 3.096 | 1.605 |
| 5 | 1.946 | 2.096 | 1.958 |
| 6 | 2.187 | 2.813 | 1.000 |
| 7 | 1.001 | 1.000 | 3.999 |
| 8 | 2.515 | 1.000 | 2.485 |
| 9 | 2.889 | 1.721 | 1.390 |
| 10 | 4.000 | 1.000 | 1.000 |
| 11 | 3.161 | 1.000 | 1.839 |
| 12 | 6.000 | 0.000 | 0.000 |
| 13 | 0.000 | 6.000 | 0.000 |
| 14 | 0.000 | 0.000 | 6.000 |

Note:
each compatible composition is consisted of quercetin-3-O-β-D-glucuronide, isoquercitrin and quercetin, and their total molar concentration is 20 μM. Table 1 shows the molar concentration ratio of the active ingredients.

I. Influence of the Drug on the Lipid Droplet Content of the Rat Primary Hepatocyte The hepatocyte is taken out from the SD rat liver by using Seglen two steps in situ circulatory perfusion method, filtered through 100-mesh sieve, centrifugated for 3 min at 500 rpm and 4° C., and the supernatant is discarded, and the hepatocyte is washed three times in the same way. The number of living cells and the cell survival rate is obtained by counting the cell, and the cells are added in the plate at $1.0*10^6$ cell/mL medium. The cells are cultured for 24 hours, then the supernatant is discarded, and the cells are washed with PBS three times. All of the cells are classified into contrast group, hyperlipidemia model group, and hyperlipidemia model+compatible composition group, wherein all of the cells of the model groups treated with hyperlipidemia are added with free fatty acid, i.e., FFA, having a final concentration of 1 mmol/L. Other groups are adjusted to a final volume of 2 mL with Williams'E medium without serum, and 24 hours after administration, washed with PBS in 37° C. three times, digested by the pancreatin, centrifugated, the supernatant is discarded, the cells are resuspended with PBS, and the final concentration is adjusted to 1 μg/mL by adding nile red dye. The fluorescence value under the exciting light of 489 nm is flow detected, and geometric median of the fluorescence intensity is used for data analysis.

The test results are shown in Table 2.

TABLE 2

Influence of compatible compositions on lipid droplet content of primary hepatocyte (means ± s.d., n = 3)

| group number | administration dose (μM) | decrease of the lipid droplet content (%) |
|---|---|---|
| 1 | 20 | 16.13 ± 0.90 |
| 2 | 20 | 33.75 ± 1.00 |
| 3 | 20 | 23.96 ± 2.46 |
| 4 | 20 | 34.31 ± 0.96 |
| 5 | 20 | 38.67 ± 0.98 |
| 6 | 20 | 24.58 ± 2.33 |
| 7 | 20 | 8.10 ± 1.19 |
| 8 | 20 | 13.13 ± 0.76 |
| 9 | 20 | 24.53 ± 3.00 |
| 10 | 20 | 37.16 ± 2.12 |
| 11 | 20 | 32.42 ± 1.10 |
| 12 | 20 | 8.07 ± 0.92 |
| 13 | 20 | 7.52 ± 1.63 |
| 14 | 20 | 7.01 ± 1.03 |

Note:
Decrease of lipid droplet content (%) = (lipid droplet content average value of the model group − lipid droplet content average value of administered group) × 100%/lipid droplet content average value of model group.

By analyzing with flow cytometry calculation, inventors found that the median representing fluorescence intensity increases with the right shift of the spectrum peak, indicating that the fluorescence intensity also increases and the content of the lipid droplet also increases, wherein the compatible groups 1 to 11 are formed by combining quercetin-3-O-β-D-glucuronide, isoquercitrin and quercetin; the compatible groups 12 to 14 are individual quercetin-3-O-β-D-glucuronide, isoquercitrin and quercetin, respectively. Compared with the individual compound groups 12 to 14, the effect of the compatible groups to decrease the lipid droplet content is better. At the same time, each of the compatible groups is different significantly in decreasing the intracellular lipid droplet content, and the effect of compatible groups 2, 3, 4, 5, 6, 9, 10 and 11 to decrease the lipid droplet is notable.

II. Analysis of Compatible Synergistic Effect of the Three Individual Compounds

TABLE 3

Analysis of compatible synergistic effect of *Cichorium glandulosum* Boiss et Hout active ingredients

| interaction term | estimated coefficient | freedom | standard error | 95% confidence lower limit | 95% confidence upper limit |
|---|---|---|---|---|---|
| A-A | −0.95 | 1 | 0.46 | −6.83 | 4.93 |
| B-B | −1.39 | 1 | 0.46 | −7.27 | 4.49 |

TABLE 3-continued

Analysis of compatible synergistic effect of *Cichorium glandulosum* Boiss et Hout active ingredients

| interaction term | estimated coefficient | freedom | standard error | 95% confidence lower limit | 95% confidence upper limit |
|---|---|---|---|---|---|
| C-C | −2.48 | 1 | 0.46 | −8.37 | 3.41 |
| AB | −2.6 | 1 | 2.49 | −34.28 | 29.08 |
| AC | 0.76 | 1 | 2.26 | −29.53 | 28.02 |
| BC | 0.92 | 1 | 2.26 | −27.75 | 29.59 |
| ABC | 31.28 | 1 | 17.46 | −190.61 | 253.16 |

In Table 3, A represents quercetin-3-O-β-D-glucuronide, B represents isoquercitrin, and C represents quercetin.

Analyzing interaction estimated coefficients in Table 3, a larger coefficient indicates stronger interaction among the compounds. It can be seen, regarding decreasing the lipid droplet content, the interaction among the three compounds quercetin-3-O-β-D-glucuronide, isoquercitrin and quercetin is the strongest, which is stronger than the interaction between every two drugs of the three, and stronger than the effect of each individual compound.

III. 3D Plot and Contour Map Used for Calculating Compatible Ratio by Response Surface Analysis Method Using D-Optimal experimental design method in the mixture experimental design, calculation is carried out by using response surface analysis method and using Design expert8.05b software. Choosing D-optimal in the Mixture option, analysis is carried out by entering compatible ratio of the compatible groups and the test results in Table 2. The test results are fitted by choosing the model which has the maximum value in the adjusted R-square and predictive R-square in the results, and the model obtained by fitting is used to predict the effect of various quercetin-3-O-β-D-glucuronide, isoquercitrin and quercetin ratio to decrease the lipid droplet content, thus 3D-response surface plot and corresponding contour map can be obtained. See FIG. 1.

Dots in the 3D plot in FIG. 1 represent test true values, and the curved surface is formed from the predictive values of quercetin-3-O-β-D-glucuronide, isoquercitrin and quercetin under various ratio. The response results in FIG. 1 are analysed, F value is 5.19, and the multiple correlation coefficient $R^2$ is 0.8862, indicating that the model fits the true situation well. The signal to noise ratio (Adeq Precision) is 8.017, indicating the high reliability, so this method can be used to predict response values.

It can be obtained from the analysis results of 3D plot that, when the molar concentration ratio among quercetin-3-O-β-D-glucuronide, isoquercitrin and quercetin is (1.1-2.4):(1.3-3.3):(1.2-3.1), the decrease of the lipid can reach 20% or more, and when the molar concentration ratio is (1.3-2.1):(1.6-3.0):(1.5-2.9), the decrease of the lipid can reach 30% or more; and when the molar concentration ratio is (1.4-1.9):(1.8-2.6):(1.8-2.6), the decrease of the lipid can reach 40% or more.

Subsequently, three points H, M and L are selected in the 3D plot from top to bottom, representing three compatible ratios with lipid-lowering effect from good to bad, respectively, and the compatible ratios of these three points is stained with oil red to carry out confirmation.

IV. Oil Red Staining Confirmation

The hepatocyte is taken out from the SD rat liver by using Seglen two steps in situ circulatory perfusion method, filtered through 100-mesh sieve, centrifugated for 3 min at 500 rpm and 4° C., and the supernatant is discarded, and the hepatocyte is washed three times in the same way. The number of living cells and the cell survival is obtained by cell count, and the cells are added in the plate at $1.0*10^6$ cell/mL medium. The cells are cultured for 24 hours, then the supernatant is discarded, and the cells are washed with PBS three times. All of the cells are classified into contrast group, hyperlipidemia model group and hyperlipidemia model+compatible composition group, wherein all of the cells of the model groups treated with hyperlipidemia are added FFA having a final concentration of 1 mmol/L. The other groups are adjusted to a final volume of 2 mL with DEME without serum, 24 hours after administration, washed with PBS in 37° C. three times, fixed with 4% paraformaldehyde for 30 min, washed with PBS three times, stained with oil red dye solution for 50 min, washed with PBS three times, and observed with 400× inverted microscope. The test results are shown in FIG. 2.

The oil red is a liposoluble dye, which can specifically stain the neutral lipid such as triglyceride in cells, so the lipid stained by the oil red in the cells can be seen under the microscope. Such property of the oil red can be used to decide the intracellular lipid content. It is demonstrated by the results of oil red staining, after giving the cell 1 mM FFA stimulation for 24 hours, in the primary hepatocyte, obvious lipid deposition occurred, which presented as lipid droplet number increasing and volume becoming larger. The positive drug bezafibrate is a PPAR-α agonist, which can decrease the intracellular lipid droplet content by promoting the oxidation of the fatty acid in cells. Compared with the model groups, all of the bezafibrate groups, the compatible groups and the individual compound groups can decrease the lipid droplet content in the rat primary hepatocyte in the hyperlipidemia model to a certain extent, and the lipid droplet content of the compatible groups H, M and L is less than that of the individual compound groups, which indicates that the lipid-lowering effect is better after combining three compounds. Furthermore, the lipid droplet content of the compatible groups H, M and L increases gradually, which is accordant with the predictive result of the 3D plot, further confirming the reliability of the built algorithm model.

V. The Influence of the Compatible Composition on the High Fat Diet Induced Rat Lipid Metabolism Disorder Model Experiment method: 90 SD rats are normally fed for 1 week, the normal group of 10 rats are fed common feedstuff, and others are fed high fat feedstuff (basic feedstuff 88%, lard 10% and cholesterol 2%). 4 weeks later, the rats fed high fat feedstuff are randomly divided into 5 groups, each group of 10. The experimental groups are as follows: ① blank control group: common feedstuff+0.5% CMC-Na; ② hyperlipidemia model group: high fat feedstuff+0.5% CMC-Na; ③ bezafibrate group (100 mg/kg): high fat feedstuff+bezafibrate; ④ compatible group 1 (100 mg/kg): high fat feedstuff+compatible composition (the molar concentration ratio among quercetin-3-O-β-D-glucuronide, isoquercitrin and quercetin is 1.968:2.551:1.481); ⑤ compatible group 2 (100 mg/kg): high fat feedstuff+compatible composition 2 (the molar concentration ratio among quercetin-3-O-β-D-glucuronide, isoquercitrin and quercetinis 1.728:2.743:1.529); ⑥ compatible group 3 (100 mg/kg): high fat feedstuff+compatible composition 3 (the molar concentration ratio among quercetin-3-O-β-D-glucuronide, isoquercitrin and quercetin is 2.128:2.479:1.393). The rats in the bezafibrate group are fed bezafibrate 100 mg/kg at the same time as the high fat feedstuff feeding respectively. The tested sample groups are given 100 mg/kg by gavage respectively at the same time as the high fat feedstuff feeding, once a day. The experiment animals can freely drink water and take food, and are fed separately in cages in light and dark for 12 hours, respectively, in a SPF grade animal lab under 25±2° C. After the eighth week of the experiment, the rats are fasted for 16 hours, collected blood from arteria cruralis, sacrificed by dislocating the cervical vertebra, taking out the liver, and preparing serum and liver tissue homogenate in conventional method. The triglyceride (TG), total cholesterol (TC), high density lipoprotein (HDL-C), low density lipoprotein (LDL-C), glutamic-pyruvic transaminase (ALT) and glutamic-oxalacetic transaminase (AST) content in the serum and liver is detected.

concentration ratio among quercetin-3-O-β-D-glucuronide, isoquercitrin and quercetin is 2.128:2.479:1.393). Except for the blank control group, all of the other groups are added FFA having a final concentration of 1 mmol/L, and the remaining volume is completed to 2 mL with the DMEM medium containing 10% fetal bovine serum, 24 hours after administration, washed with PBS in 37° C. three times, digested by the pancreatin, centrifugated, the supernatant is discarded, the cells are resuspended with PBS, and the final concentration is adjusted to 1 μg/mL by adding nile red dye. The fluorescence value under the exciting light of 489 nm is flow detected, and geometric median of the fluorescence intensity is chosen to carry out data analysis.

TABLE 4

Effect of compatible composition on high fat diet induced rat lipid metabolism disorder model

| | index | blank control group | model group | bezafibrate group (0.1 g/kg) | compatible groups 1 (0.1 g/kg) | compatible groups 2 (0.1 g/kg) | compatible groups 3 (0.1 g/kg) |
|---|---|---|---|---|---|---|---|
| serum | Weight (g) | 381.17 ± 20.06** | 443.63 ± 26.74 | 433.15 ± 24.53 | 390.53 ± 16.98** | 405.00 ± 12.49** | 412.28 ± 17.32 |
| | TC (mmol/L) | 0.87 ± 0.23** | 2.67 ± 0.47 | 1.58 ± 0.17* | 1.04 ± 0.39** | 1.58 ± 0.66* | 1.78 ± 0.66* |
| | TG (mmol/L) | 0.72 ± 0.21** | 1.92 ± 0.27 | 0.88 ± 0.19** | 0.77 ± 0.07** | 0.92 ± 0.21* | 1.13 ± 0.23* |
| | HDL-C (mmol/L) | 1.77 ± 0.19* | 1.12 ± 0.21 | 1.58 ± 0.29* | 1.52 ± 0.13* | 1.30 ± 0.28* | 1.24 ± 0.19* |
| | LDL-C (mmol/L) | 0.45 ± 0.18** | 2.20 ± 0.50 | 0.54 ± 0.30** | 0.53 ± 0.12** | 0.83 ± 0.30** | 0.91 ± 0.22** |
| liver | ALT (U/L) | 96.1 ± 12.82** | 268.0 ± 17.01 | 107.9 ± 14.12** | 112.8 ± 10.07** | 119.34 ± 14.28** | 126.14 ± 12.29** |
| | AST (U/L) | 200.8 ± 26.87** | 337.0 ± 58.06 | 217.8 ± 33.93** | 207.0 ± 14.71** | 225.8 ± 26.72** | 240.3 ± 27.12* |
| | TC (mg/g liver) | 31 ± 11.13* | 52 ± 9.86 | 33 ± 12.23* | 40 ± 10.01* | 42 ± 9.98* | 44 ± 11.17* |
| | TG (mg/g liver) | 179 ± 33.36* | 258 ± 37.86 | 186 ± 37.92* | 183 ± 50.43* | 197 ± 47.33* | 204.30 ± 30.81* |

Compared with the model group, *P < 0.05, P < 0.01 and *P < 0.001.

Analysis: compared with the blank control group, the weight, TG, TC, ALT and AST content of the model group increase notably, and the difference is large, indicating that the rat lipid metabolism disorder model has been established successfully. Compared with the model group, bezafibrate group, compatible group 1, compatible group 2 and compatible group 3 can decrease the weight, TG, TC, ALT, AST and HDL-C content in various degree, and increase the LDL-C content, indicating that the compatible groups has lipid-lowering protection effect, wherein the efficacy of the compatible composition 1 is best, better than that of the compatible composition 2 and the compatible composition 3.

VI. The Influence of the Compatible Composition on the Lipid Droplet Content of the Free Fat Acid (FFA) Induced HepG2 Cell Experiment method: the HepG2 cells in the logarithmic growth phase are taken having a growth density of 80%, and inoculated into 6-well plate at 1×10⁵ per well. After culturing cells for 24 hours, the supernatant is discarded, and the cells are washed with PBS three times. The cells are divided into: ① the blank control group: 0.1% DMSO; ② the model group: 1 mM FFA; ③ the bezafibrate group (100 μM): 100 μM bezafibrate; ④ the compatible group 1 (100 mg/kg): 1 mM FFA+compatible composition 1 (the molar concentration ratio among quercetin-3-O-β-D-glucuronide, isoquercitrin and quercetin is 1.968:2.551:1.481); ⑤ the compatible group 2 (100 mg/kg): 1 mM FFA+compatible composition 2 (the molar concentration ratio among quercetin-3-O-β-D-glucuronide, isoquercitrin and quercetin is 1.728:2.743:1.529); ⑥ the compatible group 3 (100 mg/kg): 1 mM FFA+compatible composition 3 (the molar

TABLE 5

Influence of compatible compositions on lipid droplet content of FFA induced HepG2 cells (means ± s.d., n = 3)

| group number | administration dose (μM) | lipid droplet content |
|---|---|---|
| blank control group | — | 107.81 ± 4.90*** |
| model group | — | 222.64 ± 8.34 |
| bezafibrate group | 100 | 178.84 ± 2.84*** |
| compatible group 1 | 20 | 131.92 ± 3.96*** |
| compatible group 2 | 20 | 139.25 ± 4.98*** |
| compatible group 3 | 20 | 149.70 ± 2.33*** |
| quercetin-3-O-β-D-glucuronide | 20 | 153.38 ± 2.88*** |
| isoquercitrin | 20 | 200.61 ± 8.43** |
| quercitrin | 20 | 198.25 ± 6.04** |

Compared with the model group,
*P < 0.05,
**P < 0.01,
***P < 0.001.
The ratio of the compatible groups is the molar concentration ratio among each component, and the total molar concentration of all the compatible groups is 20 μM.

Analysis: the positive drug bezafibrate is a PPAR-α agonist, which can decrease the intracellular lipid droplet content by promoting the oxidation of the fatty acid in cells. Compared with the model groups, all of the bezafibrate groups, the compatible groups and the individual compound groups can decrease the lipid droplet content in the 1 mM FFA stimulated HepG2 cells to a certain extent, and such efficacy of the compatible group 1 is better that of other compatible groups. Compared with the individual compound groups, the effect of the compatible groups to decrease the intracellular lipid droplet content is more obvious, which indicates that combining quercetin-3-O-β-D-glucuronide, isoquercitrin and quercetin can bring about synergistic effect.

DESCRIPTION OF THE PREFERRED EMBODIMENTS

Figure 1:
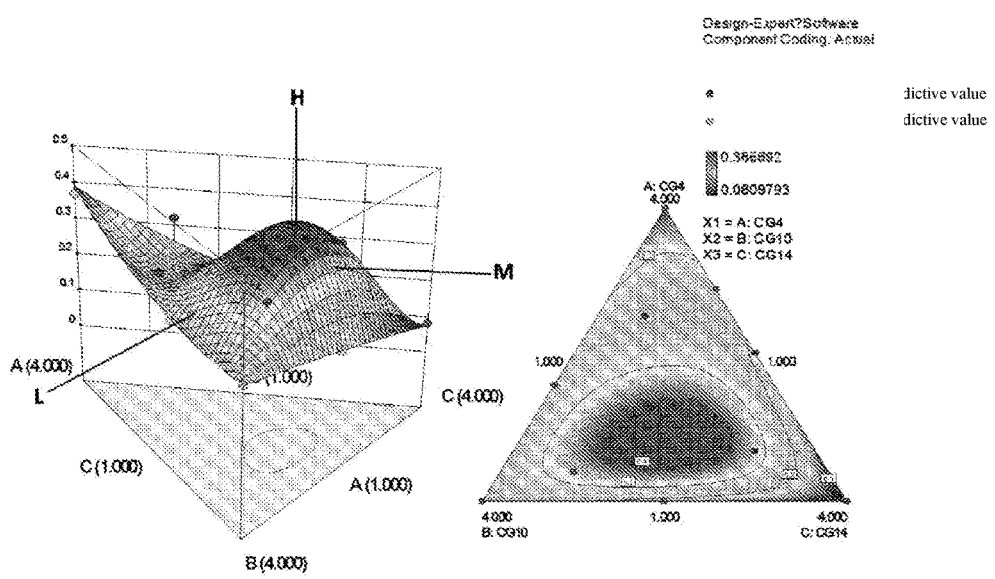
FIG. 1 is the 3D kyrtograph and contour map of the lipid droplet content inhibition ratio of the compatible groups (CG4:quercetin-3-O-β-D-glucuronide, CG10:isoquercitrin, CG14:quercetin)
Figure 2:
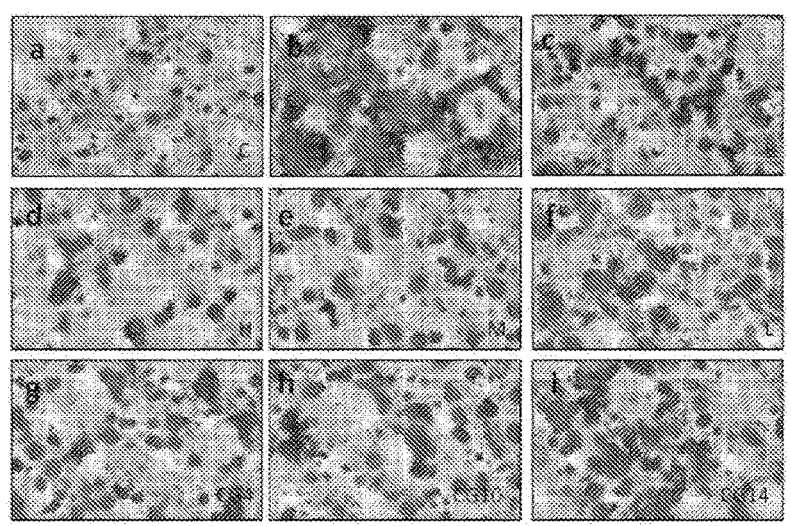
FIG. 2 is FFA induced rat primary hepatocyte hyperlipidemia model which is stained by oil red (400×), (a) control group; (b) model group; (c) positive drug bezafibrate 100 µM; (d) H: the molar concentration ratio among quercetin-3-O-β-D-glucuronide, isoquercitrin and quercetin is 1.946:2.096:1.958; (e) M: the molar concentration ratio among quercetin-3-O-β-D-glucuronide, isoquercitrin and quercetin is 1.661:1.322:3.018; (f) L: the molar concentration ratio among quercetin-3-O-β-D-glucuronide, isoquercitrin and quercetin is 2.072:2.878:1.050; (g) CG4: quercetin-3-O-β-D-glucuronide 20 µM; (h) CG10: isoquercitrin 20 µM; (i) CG14: quercetin 20 µM.

Below, preferred embodiments of the present invention are explained.

First Embodiment

| Tablet | |
|---|---|
| quercetin-3-O-β-D-glucuronide | 121.0 mg |
| isoquercitrin | 152.0 mg |
| quercetin | 57.0 mg |
| lactose | 90.0 mg |
| starch | 38.0 mg |
| carboxymethyl starch sodium | 20.0 mg |
| avicel | 20.0 mg |
| dolomol | 2.0 mg |
| total | 500 mg |

The feeding capacity is 1000 tablets, and the components of each tablet are listed in the above table. The powder is mixed, and compressed by the tablet machine, to make the tablet of 500 mg.

Second Embodiment

| Tablet | |
|---|---|
| quercetin-3-O-β-D-glucuronide | 106.0 mg |
| isoquercitrin | 164.0 mg |
| quercetin | 60.0 mg |
| lactose | 90.0 mg |
| starch | 38.0 mg |
| carboxymethyl starch sodium | 20.0 mg |
| avicel | 20.0 mg |
| dolomol | 2.0 mg |
| total | 500 mg |

The preparation method is the same as Example 1.

Third Embodiment

| Tablet | |
|---|---|
| quercetin-3-O-β-D-glucuronide | 130.0 mg |
| isoquercitrin | 147.0 mg |
| quercetin | 53.0 mg |
| lactose | 90.0 mg |
| starch | 38.0 mg |
| carboxymethyl starch sodium | 20.0 mg |
| avicel | 20.0 mg |
| dolomol | 2.0 mg |
| total | 500 mg |

The preparation method is the same as Example 1.

What is claimed is:

1. A method of treating a lipid metabolism disorder disease, the method comprising administering to a patient in need a compound pharmaceutical composition, comprising pharmaceutical active ingredients and pharmaceutically accepted carrier, wherein the pharmaceutical active ingredients consist of quercetin-3-O-β-D-glucuronide, isoquercitrin and quercetin at a molar ratio of 1.1-2.4:1.3-3.3:1.2-3.1, wherein the lipid metabolism disorder disease is selected from the group consisting of obesity, fatty liver, atherosclerosis and hyperlipoprotememia.

2. The method according to claim 1, wherein the molar ratio among quercetin-3-O-β-D-glucuronide, isoquercitrin and quercetin is 1.3-2.1:1.6-3.0:1.5-2.9.

3. The method according to claim 2, wherein the molar ratio among quercetin-3-O-β-D-glucuronide, isoquercitrin and quercetin is 1.4-1.9:1.8-2.6:1.8-2.6.

* * * * *